United States Patent [19]

Gordon et al.

[11] 4,046,823

[45] Sept. 6, 1977

[54] PROCESS FOR PRODUCING 1,2-DICHLOROETHANE

[75] Inventors: Ronnie D. Gordon; Charles M. Starks, both of Ponca City, Okla.

[73] Assignee: Continental Oil Company, Ponca City, Okla.

[21] Appl. No.: 124,441

[22] Filed: Mar. 15, 1971

[51] Int. Cl.$^2$ .............................................. C07C 17/10
[52] U.S. Cl. ............................ 260/662 R; 260/658 R
[58] Field of Search ........................ 260/658 R, 662 R

[56] References Cited

U.S. PATENT DOCUMENTS

| 2,010,039 | 8/1935 | Sharp | 260/658 R |
|---|---|---|---|
| 2,838,579 | 6/1958 | Conrad et al. | 260/662 R |
| 3,138,643 | 6/1964 | Taylor et al. | 260/658 R |
| 3,166,602 | 1/1965 | Taylor | 260/662 R |
| 3,304,337 | 8/1962 | Jordan et al. | 260/662 R |
| 3,720,723 | 3/1973 | Pritchett | 260/658 R |

FOREIGN PATENT DOCUMENTS

| 492,175 | 3/1919 | France | 260/658 R |

OTHER PUBLICATIONS

Kirk-Othmer, *Encyclopedia of Chemical Technology*, vol. 6, 1965, pp. 271 and 272.

*Primary Examiner*—Delbert E. Gantz
*Assistant Examiner*—Joseph A. Boska
*Attorney, Agent, or Firm*—Ronald J. Carlson

[57] ABSTRACT

1,2-dichloroethane is produced by reacting, in a vapor phase, chlorine and ethane in the presence of a copper containing catalyst at a temperature in the range of from about 200° to about 500° C.

7 Claims, No Drawings

PROCESS FOR PRODUCING 1,2-DICHLOROETHANE

BACKGROUND OF THE INVENTION

1. Field of the Invention

The present invention relates to the production of 1,2-dichloroethane. More particularly, but not by way of limitation, the present invention relates to the production of 1,2-dichloroethane by direct chlorination of ethane with chlorine gas in the presence of a copper containing catalyst.

2. Brief Description of the Prior Art 1,2-dichloroethane is a well known intermediate employed in the production of vinyl chloride monomer. It has been known that ethane could be chlorinated to yield compounds such as ethyl chloride, mixtures of the dichloroethanes, and even higher chlorinated compounds such as the triochloroethanes. However, in most of the processes described in the prior art, it has not been possible to produce, 1,2-dichloroethane by the direct chlorination of ethane. For example, heretofore, it has been known in the art that chlorination of ethane with molecular chlorine at high temperatures of about 300° C resulted in products predominantly of 1,1-dichloroethane and ethylene chloride. Other problems had been encountered in the prior art methods such as undesired carbon deposits which occur in the reaction zone or the formation of undesired by-products due to pyrolysis of the chloroethane products. Thus, the prior art methods have turned to other areas such as the production of 1,2-dichloroethane from a reaction of chlorine and ethylene. Therefore, a practical, simple process for the chlorination of ethane to 1,2-dichloroethane has long been needed.

OBJECTS OF THE INVENTION

An object of the present invention is to produce 1,2-dichloroethane. Another object of the present invention is to produce 1,2-dichloroethane directly from ethane.

These and other objects, features, and advantages of the present invention will be apparent to those skilled in the art from the reading of the following detailed description.

SUMMARY OF THE INVENTION

According to the present invention we have now discovered that 1,2-dichloroethane can be produced by the direct chlorination of ethane with chlorine gas when such chlorination is carried out in the presence of a copper containing catalyst. Further according to the invention we have found that 1,2-dichloroethane can be produced by reacting, in a vapor phase, chlorine and ethane in the presence of a copper containing catalyst at a temperature in a range from about 200° to about 500° C when the chlorine and ethane are present in a molar ratio of from about 1:10 to about 10:1, respectively.

DESCRIPTION OF THE PREFERRED EMBODIMENTS

The present invention relates to a process for producing 1,2-dichloroethane by the direct chlorination of ethane with chlorine gas in the presence of a copper containing catalyst. The reaction conditions, such as temperature and pressure can vary widely, the major requirement being that the ethane and chlorine are to be in a vapor phase. Generally, the process will be conducted at atmospheric pressure and at a temperature within the range from about 200° to about 500° C. Especially desirable results have been obtained wherein the reaction is carried out at atmospheric pressure and at a temperature in the range of from about 280° to about 350° C. In the practice of the invention it is generally desired to pass the gaseous mixture of ethane and chlorine through a heated catalyst zone containing the copper containing catalyst so that the ethane can be directly chlorinated with the chlorine gas. The amount of ethane and chlorine can vary widely but generally the chlorine and ethane are present in a molar ratio of from about 1:10 to about 10:1, respectively. Desirable results have been obtained wherein the molar ratio of chlorine to ethane is in the range of about 1:1 to about 1:5. In carrying out the process of the present invention it is often advantageous to incorporate an inert gas into the mixture of the chlorine and ethane to enable one to more readily control the process and thus the production of 1,2-dichloroethane. Any suitable inert gas which will not interfere with the direct chlorination of the ethane to 1,2-dichloroethane can be employed. Generally, the inert gas will be admixed in an amount sufficient to provide a ratio of about 1:1 to about 20:1 moles of the inert gas per mole of ethane. Examples of suitable inert gases which can be employed are nitrogen, argon, helium, methane, carbon dioxide, steam, and hydrogen chloride.

The ethane employed to produce the 1,2-dichloroethane of the present invention is generally desired to be in as pure a state as possible to prevent formation of undesirable by-products and thus create problems, such as the separation of the 1,2-dichloroethane from these by-products. However, we have found that ethyl chloride can be incorporated into the ethane feed without adversely affecting the formation of the 1,2-dichloroethane. When ethyl chloride is present in the ethane feedstream it is generally desired that same be present in molar ratio from about 1:1 to 10:1 with respect to the ethane.

The copper catalyst employed in the present invention can be any suitable copper containing catalyst which will aid in the formation of 1,2-dichloroethane by the direct chlorination of ethane. Generally, the copper containing catalyst is an alumina supported catalyst wherein the catalyst constituent is selected from the group consisting of $CuCl_2$ and $CuO$. In addition, it has been found advantageous to include catalyst promoters such as KCl and inorganic iron salts in the copper containing catalyst to aid in the direct chlorination of the ethane. Examples of suitable inorganic iron salts which can be employed as catalyst promoters are $FeCl_3$ and $Fe_2O_3$.

In order to more fully describe the present invention the following example is given. However, it should be understood that the example is for illustrative purposes only and is not intended to unduly limit the invention as disclosed herein.

EXAMPLE 170 grams of a cupric chloride on alumina catalyst in the form of ⅛ inch pellets was charged to a Pyrex glass reactor having the dimensions of 250 mm × 50 mm. The reactor was heated until the temperature of the catalyst reached 300° C. Chlorine, ethane, and nitrogen were mixed in ratios of 1:3:12 and passed through the reactor and thus, in contact with the catalyst which was maintained at a temperature of about 300° C. The total flow rate of the gases was about 1.3 liters per hour. The effluent from the reactor was then collected in a dry ice-isopropanol trap and analyzed by gas chromatography. The analysis confirmed that 50% of the ethane had been converted to 1,2-dichloroethane. Further, the analytical data illustrated that ethane can be directly chlorinated to 1,2-dichloroethane in the presence of a copper containing catalyst with a selectivity for the 1,2-dichloroethane of over 95%.

Having thus described the invention, we claim:

1. A process for producing 1,2-dichloroethane which comprises reacting chlorine and ethane in the vapor phase at temperatures in the range of 200° to 500° C in the presence of an alumina supported cupric catalyst promoted with a member selected from the group consisting of KCl and inorganic iron salts, said cupric constituent being selected from the group consisting of $CuCl_2$ and CuO, the mol ratio of chlorine to ethane being in the range of 1:10 to 10:1.

2. The process of claim 1 which includes an inert gas and said inert gas is present, with respect to said ethane, in a molar ratio of about 1:1 to about 20:1.

3. The process of claim 2 wherein said inert gas is selected from the group consisting of nitrogen, argon, helium, methane, carbon dioxide, steam and hydrogen chloride.

4. The process of claim 1 wherein said iron salts are $FeCl_3$ and $Fe_2O_3$.

5. The process of claim 1 wherein said reaction is carried out at a temperature range of from about 280° to about 350° C and said chlorine and ethane are present in a molar ratio of from about 1:1 to 1:5, respectively.

6. The process of claim 5 which includes nitrogen as an inert gas, said chlorine, ethane, and nitrogen being present in a molar ratio of about 1:3:12, respectively, and said catalyst is $CuCl_2$ supported on alumina.

7. The process of claim 1 which includes ethyl chloride admixed with said ethane and said ethyl chloride is present, with respect to said ethane, in a molar ratio of about 1:1 to 10:1.

* * * * *